United States Patent [19]

Tacchi

[11] 4,248,241
[45] Feb. 3, 1981

[54] PATIENT MONITORING APPARATUS

[76] Inventor: Ernest J. Tacchi, 500 Duluth St., Durham, N.C. 27705

[21] Appl. No.: 67,389

[22] Filed: Aug. 17, 1979

Related U.S. Application Data

[63] Continuation-in-part of Ser. No. 893,428, Apr. 4, 1978, abandoned.

[51] Int. Cl.³ .............................................. A61B 5/00
[52] U.S. Cl. .................................. 128/671; 128/685; 128/686; 128/715; 128/903
[58] Field of Search .............................. 128/670–671, 128/680–686, 715, 773, 903; 179/1 ST; 181/131; 340/177 R, 177 CA

[56] References Cited

U.S. PATENT DOCUMENTS

| | | | |
|---|---|---|---|
| 2,699,465 | 1/1955 | Hamilton | 128/715 |
| 3,513,832 | 5/1970 | Klemm et al. | 128/671 |
| 3,517,664 | 6/1970 | Ploss | 128/685 |
| 3,552,381 | 1/1971 | Burns et al. | 128/683 |
| 3,646,606 | 2/1972 | Buxton et al. | 128/670 |
| 4,005,506 | 2/1977 | Moore | 128/DIG. 15 X |
| 4,072,822 | 2/1978 | Yamada | 179/1 ST |

FOREIGN PATENT DOCUMENTS 1008027 10/1965 United Kingdom .................... 128/715

OTHER PUBLICATIONS

Ploss, R. E., "A Simple Constant Monitor System", Anesthesiology, vol. 16 (1955) pp. 466–467.

Primary Examiner—Robert W. Michell
Assistant Examiner—Francis J. Jaworski
Attorney, Agent, or Firm—B. B. Olive

[57] ABSTRACT

A patient monitoring apparatus employs transmitter and receiver units. The transmitter unit is typically mounted on the patient and is equipped with an inflatable blood pressure cuff having an associated acoustic stethoscope pickup piece for detecting the systolic and diastolic pressure related sounds which may be selectively and pneumatically coupled to the transmitter unit for radio broadcast to the receiver unit. The transmitter unit may also be selectively coupled to conventional stethoscope ear pieces and sound pickup pieces which can be either chest, esophagus, or otherwise mounted on the patient to detect the sounds generated by and/or associated with respiratory and cardiac functions. Thus, sounds related to either blood pressure determination or cardiorespirtory auscultation can be detected by the transmitter unit and broadcast to the receiver unit. The receiver unit is typically belt or pocket mounted on the attending anesthetist. Two switching systems are illustrated, either of which may be utilized to enable the anesthetist to automatically select which sound, i.e., blood pressure or cardiorespiratory, to monitor. On-off transmitter control as well as battery tests and channel confirmation functions are provided.

17 Claims, 10 Drawing Figures

U.S. Patent Feb. 3, 1981 Sheet 1 of 4 4,248,241
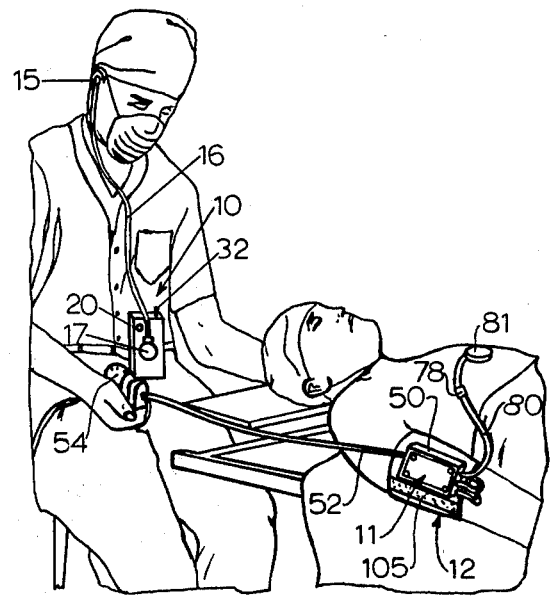
FIG. 1
FIG. 2
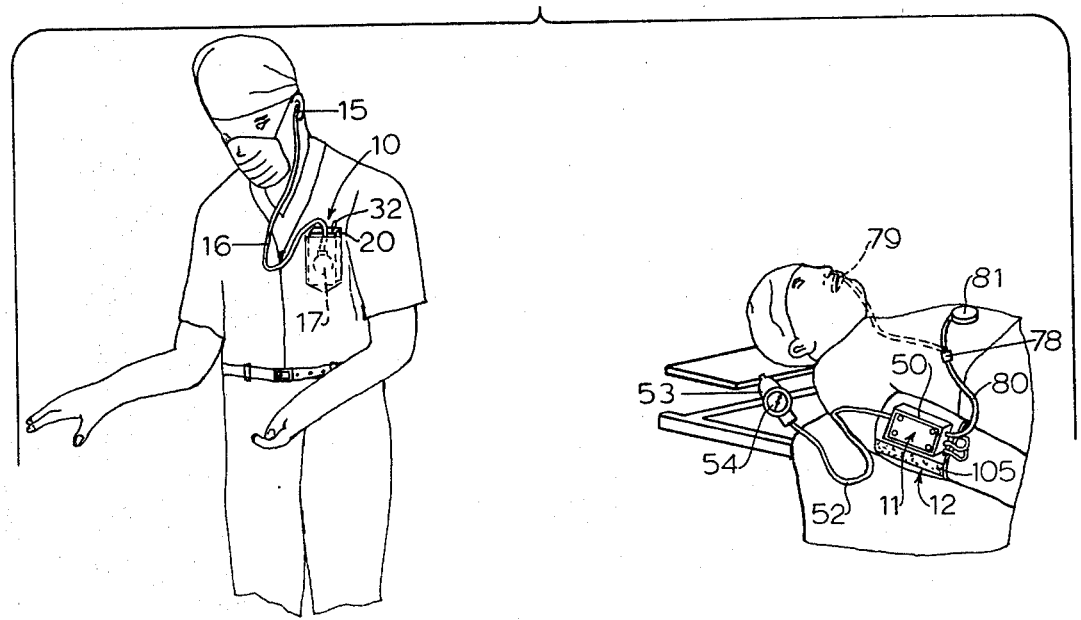

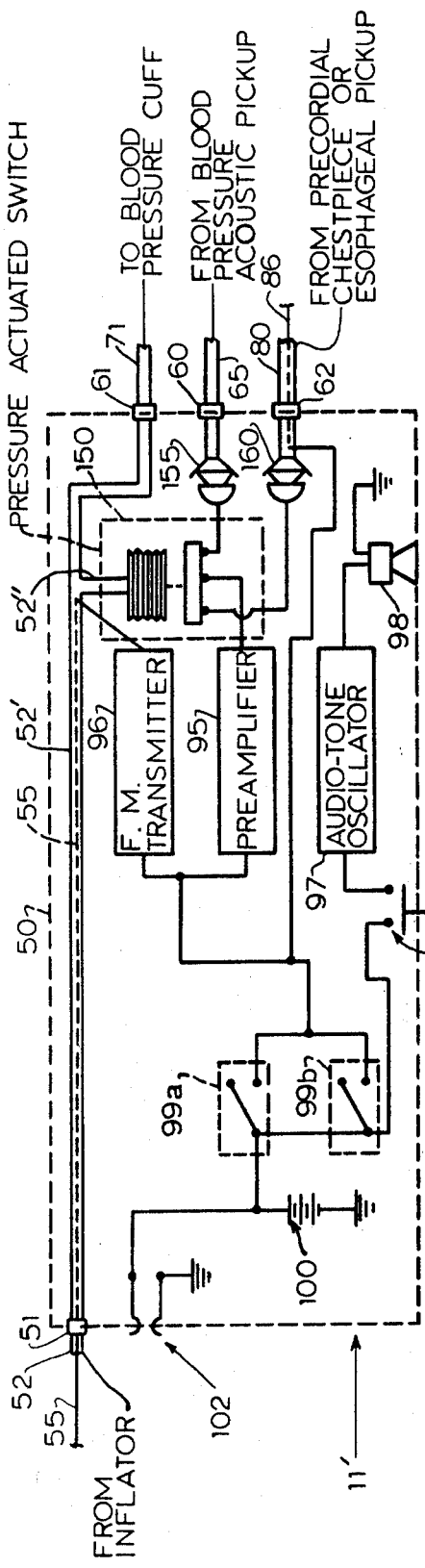
FIG. 8
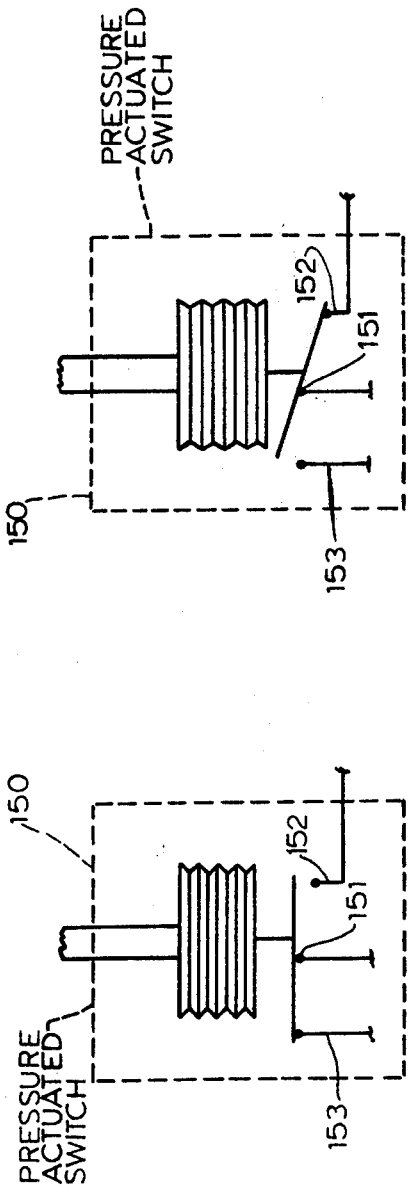
FIG. 9
FIG. 10

PATIENT MONITORING APPARATUS

CROSS-REFERENCE TO RELATED APPLICATION

This application is a continuation-in-part of copending application Ser. No. 893,428, filed Apr. 4, 1978, entitled "PATIENT MONITORING APPARATUS", now abandoned.

BACKGROUND OF THE INVENTION

1. Field of the Invention:

The invention relates to apparatus for monitoring body conditions and more specifically to an electromechanical apparatus specifically useful for monitoring sounds related to systolic and diastolic pressure measurements as well as sounds related to the heartbeat and respiratory functions.

2. Description of the Prior Art:

During the course of a majority of surgical procedures, sterile drapes often limit the anesthetist's ability to observe the thorax and patency of the airway. For this and other reasons, anesthetists have come to rely heavily upon auditory monitoring, such as through a stethoscope sound pickup piece placed on the chest wall, precordial, or placed in the esophagus, esophageal, directly behind the trachea or "windpipe". Besides indicating heart rate, the amplitude and frequency of the heart sounds detected by the use of a stethoscope sound pickup piece placed on the chest or in the esophagus will also allow some estimate of the force of cardiac contraction. A stethoscope and associated sound pickup piece is also used to detect and transmit the low frequency and low amplitude sounds associated with conventional "indirect" systolic and diastolic blood pressure determinations. Thus, the stethoscope has become an important diagnostic tool and has gained importance in the course of anesthetic management during both major and minor surgical procedures.

Various electronic stethoscope systems are illustrated in U.S. Pat. Nos. 3,087,016; 3,160,708; 3,790,712; 3,985,121 and 3,989,895. It has also been known to provide electronic apparatus to monitor selected body conditions, develop corresponding electrical signals and broadcast such signals to a receiver unit to be heard by an anesthetist or for transmission to recording apparatus or the like. U.S. Pat. No. 3,552,381 describes an apparatus designed to automatically determine, transmit and display information concerning the patient's physiologic status. No means are provided by which the operator's senses may be used to aid in clinical assessment of the patient's physiologic response to anesthesia. Other shortcomings in the apparatus of U.S. Pat. No. 3,552,381 are also to be noted in that the electronic detector is required to be in intimate contact with the patient whereas it would be desirable to shield the fragile and expensive microphone sound detector from mechanical stress and damage as with the present invention.

Special note should be taken that medical institutions throughout the world have a very sizable investment in precordial, esophageal and pneumatic blood pressure cuff stethoscope equipment. Such institutions also have a substantial investment in assocaited inflation and pressure gauge apparatus. For example, the already owned inflation apparatus may incorporate expensive mechanical, electronic, automatic or semi-automatic components or combinations of the same. Additionally, substantial investments have been made in medical institutions in pressure gauge equipment which may involve expensive mechanical, electronic or fluidic components. Thus, it would be highly desirable to have a transmitter unit which could be utilized with any of the already owned and often expensive stethoscope equipment and inflation and pressure gauge apparatus. In this regard, it may be noted that none of the apparatus described in the mentioned United States patents are adapted to operate already available stethoscope, inflation and pressure apparatus. Play apparatus, e.g., U.S. Pat. No. 4,155,196 is also noted.

Another deficiency in the prior art is to be noted in the fact that the prior art telemetry apparatus tends to produce artificial rather than natural biological sounds. British Pat. No. 1,008,027 published Oct. 22, 1965, for example, teaches a telemetry system in which the output of the microphone is amplified and manipulated to reproduce artificial and simulated low level biological sounds. However, medical practitioners have little desire or need for monitoring devices which artificially alter their perception of diagnostic information. What is needed is a portable system which allows for remote and faithful reproduction of biological sounds of diagnostic importance and the system, in effect, should be an extension of the operator's own senses. Further, the preferred system should not require the presence of an electronic pickup device in intimate contact with the patient as in the British patent or as in U.S. Pat. No. 3,552,381. Further, it would be desirable to have a portable system of the kind mentioned which allows for the intermittent detection of two biological sound sources, namely, heart and breath sounds as one source and blood pressure related Korotkoff sounds as another source and to accomplish the same automatically dependent upon inflation of a pressure cuff associated with the system. Compare, for example, the complex wired input telemetry of U.S. Pat. No. 3,646,606.

Recognition should also be made of another prior art device described in U.S. Pat. No. 3,517,664 and known as a Ploss automatic switch valve which has been uniquely incorporated in one form of the patient monitoring apparatus of the present invention. The Ploss automatic switch valve represents a commercially available pressure operated switching valve sold by Medical Production Division, Minnesota Mining and Manufacturing company of St. Paul, Minnesota, and is conventionally sold for operation in conjunction with standard blood pressure cuffs and manometers and automatic cuff inflation systems. Such a Ploss valve has five tubular connections to the valve. One connection provides a sound output to the anesthetist's monaural or binaural earpiece. A second connection is used to receive pressure from a manometer or semi-automatic inflator whenever it is desired to inflate the cuff. A third connection receives blood pressure related sounds from a blood pressure acoustic pickup. A fourth connection provides an outlet for pressure going to the blood pressure cuff. The fifth connection provides means for receiving sounds from an acoustic precordial or esophageal stethoscope. While the Ploss valve provides a greatly improved system for monitoring either precordial or esophageal sounds, the anesthetist's mobility is physically restricted. In addition, the discomfort of wearing a binaural and/or specially fitted earpiece, the annoyance of a work area cluttered with tubing (e.g., stethoscopes, intravenous fluid lines, naso-gastric tubes, Foley catheters, et cetera) and the extraneous noises produced and amplified by the stethoscope lines getting tangled up and/or hitting other equipment can approach the point of being almost unbearable. Nevertheless, the Ploss-type valve offers many valuable features useful for remote monitoring. So far as is known, however, the Ploss-type valve has never heretofore been used advantageously in a radio-type monitoring system.

As will be noted from the later detailed description of the invention, advantage is taken of using a sound transmitting tube as a means for mounting and enclosing the antenna. In this regard, it may be noted that U.S. Pat. No. 4,072,822 teaches the practice of embedding an electric wire in a specially constructed sound tube associated with a stethoscope. However, this prior art construction has two noticeable disadvantages. First, a special tube is required to be molded and, secondly, if the embedded wire breaks, the entire tubing structure is rendered useless. Thus, it would be desirable in a stethoscope system to have a construction in which a radio antenna can be both mounted and loosely enclosed within the lumen of a sound tube without incurring either of these disadvantages.

As a final aspect of the prior art, the later detailed description of the invention involves the use of Velcro material as a fastening device for the transmitter unit. This aspect of the invention leads to the observation that the prior art telemetry and electronic stethoscope apparatus appears to have given essentially no attention to the rather important aspect of providing a means for releasably posistioning the transmitter unit near the patient but in a manner which allows the normal operating procedures to go on without interference by the transmitter location. A more specific observation can be made to the effect that the prior art has not heretofore taught or suggested a practical means for releasably securing the transmitter unit to the blood pressure cuff.

With the above brief description and limitations of the prior art in mind, there remains a need to provide a radio frequency transmitter-receiver patient monitoring system which allows the operator to selectively receive either blood pressure related sounds or heartbeat and respiratory related sounds and in a manner compatible with both normal operating procedures and patient care. The providing of such a system thus becomes the object of the present invention. Other objects will appear as the description proceeds.

SUMMARY OF THE INVENTION

The patient monitoring system of the invention incorporates a receiver unit which is conveniently worn on the anesthetist's belt or in a pocket, a transmitter unit which is located on the patient on the operating table, and a pressure cuff on which the transmitter unit is releasably mounted. The receiver unit has a detachable earpiece connected by a small flexible tube to the receiver-speaker. The tube serves to transmit sound from the receiver-speaker to the earpiece and also serves as a means of mounting and enclosing the radio reception antenna within the lumen of the tube.

The transmitter housing mounts and encloses the transmitter electronics and also mounts and encloses in one embodiment a pressure actuated Ploss automatic switch valve and in another embodiment a pressure actuated electromechanical switching device. When the Ploss-type valve is utilized in the first embodiment of the invention, this combination pneumatic-acoustic valve enables the inflator to pressurize the cuff and when so pressurized to utilize a sound path through the Ploss valve and between the cuff acoustic pickup and a single transmitter microphone. When the cuff is pressurized and inflated, a sound path between the chest or esophagus mounted stethoscope acoustic pickup and the transmitter microphone is blocked but such path is opened when the cuff is deflated. Thus, when a blood pressure determination is being made, the Ploss automatic switch valve operates so as to allow the microphone to hear blood pressure related sounds and to transmit such sounds to the receiver unit for monitoring by the anesthetist. However, when blood pressure is not being measured, no pressure related sounds are generated and Ploss automatic switch valve acts to automatically establish a sound connection between the chest or esophagus mounted stethoscopy sound pickup piece to the transmitter microphone such that these sounds can be transmitted by the transmitter unit to the receiver unit for monitoring and clinical interpretation. No electronic detector contacts the patient.

In an alternate embodiment of the invention, the pressure actuated Ploss automatic switch valve is replaced with a pressure actuated switching device. In this alternate embodiment, the transmitter housing mounts and encloses the transmitter electronics as with the first embodiment and also mounts and encloses two separate microphone elements with associated sound transmitting tubes, one pressure actuated single pole, double throw switch and a pneumatic tube which connects the pressure actuated switch to the blood pressure cuff inflation system. By communicating through associated sound transmitting tubes, one microphone possesses an estabilished sound connection with the blood pressure cuff acoustic stethoscope pickup piece while the other microphone has an established sound connection with the chest or esophagus mounted acoustic stethoscope. The audio frequency electronic output of each microphone element is connected to one or the other of the switch poles of the pressure actuated switching device. The center tap or wiper blade terminal of the pressure actuated switch is coupled to the amplification and radio frequency transmission circuitry. The piston and/or diaphragm which mechanically drives the switching device is pneumatically linked to the blood pressure cuff inflation system. In this way, the radio frequency transmission circuitry is selectively coupled to the electronic signals from one or the other of the microphone elements depending on the status of the pressure actuated switch mechanism controlled by inflation or deflation of the blood pressure cuff. When the blood pressure cuff is inflated, the electronic connection between the radio frequency transmission circuitry and the microphone element associated with the chest or esophagus mounted acoustic stethoscope is opened. However, the electronic connection between the radio frequency transmission circuitry and the microphone element associated with the chest or esophagus mounted acoustic stethoscope is opened. However, the electronic connection between the radio frequency transmission circuitry and the microphone element associated with the blood pressure cuff mounted acoustic stethoscope is closed. Thus, in the alternate embodiment of the invention, when a blood pressure determination is being made, the pressure actuated switching device operates to interrupt the detection, amplification and transmission of sounds associated with cardiorespiratory function while simultaneously allowing for the normal detection, amplification and radio frequency transmission of blood pressure related sounds to the receiver unit for monitoring by the anesthetist. However, when blood pressure is not being measured, the pressure actuated switching device acts to interrupt the detection, amplification and transmission of blood pressure related sounds while simultaneously allowing for the normal detection, amplification and radio frequency transmission of sounds associated with cardiorespiratory function. Thus, the sounds of biologic function are selectively and automatically broadcast to the receiver unit for monitoring and clinical interpretation.

Applicable to both embodiments of the invention, the transmitter unit also includes a pair of magnet positionable reed switch arrangements which control energization of the transmitter unit and which are activated by placing the transmitter unit adjacent a magnetized ferrous bar embedded in the cuff unit at one position and which can be de-activated by moving the transmitter unit to another position on the cuff which allows the magnet positionable reed switch arrangement to return to an off position. Both the transmitter unit and the cuff unit have mating Velcro surfaces to facilitate this detachable positioning and switching arrangement. Such arrangement avoids the need for a separate mounting arrangement for the transmitter unit, facilitates cleaning end exhibits substantial mechanical stability and life.

The transmitter unit is also equipped with a battery recharging circuit and a battery test and signal circuit arrangement. Another unique feature associated with the transmitter unit is that the pressure tube between the inflator and the transmitter and the air tube between the chest or esophagus stethoscope sound pickup piece and the transmitter unit are employed to mount and enclose the transmitting antenna. While this mounting arrangement for the antenna has many advantages, the receiver unit and transmitter unit antenna may, however, be constructed in a manner allowing for installation within the receiver and transmitter housings respectively.

DESCRIPTION OF THE DRAWINGS

FIG. 1 is a perspective view applicable to both embodiments of the system of the invention in use at a time when blood pressure sounds are being monitored with the receiver being mounted on the belt of the anesthetist.

FIG. 2 is another perspective view applicable to both embodiments illustrating use of the system for remote monitoring of chest sounds shown in solid lines and for remote monitoring of esophageal sounds shown in dashed lines with the receiver being mounted in the shirt pocket of the anesthetist.

FIG. 8 is a block diagram of the transmitter unit according to a second embodiment.

FIG. 9 is a diagram of the pressure switch used with the transmitter unit of FIG. 8 in the position assumed when the cuff is not pressurized.

FIG. 10 is similar to FIG. 8 illustrating the pressure switch in the position assumed when the cuff is pressurized.

DESCRIPTION OF THE PREFERRED EMBODIMENT

The system of the invention incorporates a receiver unit generally designated 10 used in both of the described embodiments, a transmitter unit generally designated 11 in the first embodiment and 11' in the second embodiment, and a cuff unit generally designated 12 used in both embodiments.

Figure 4:
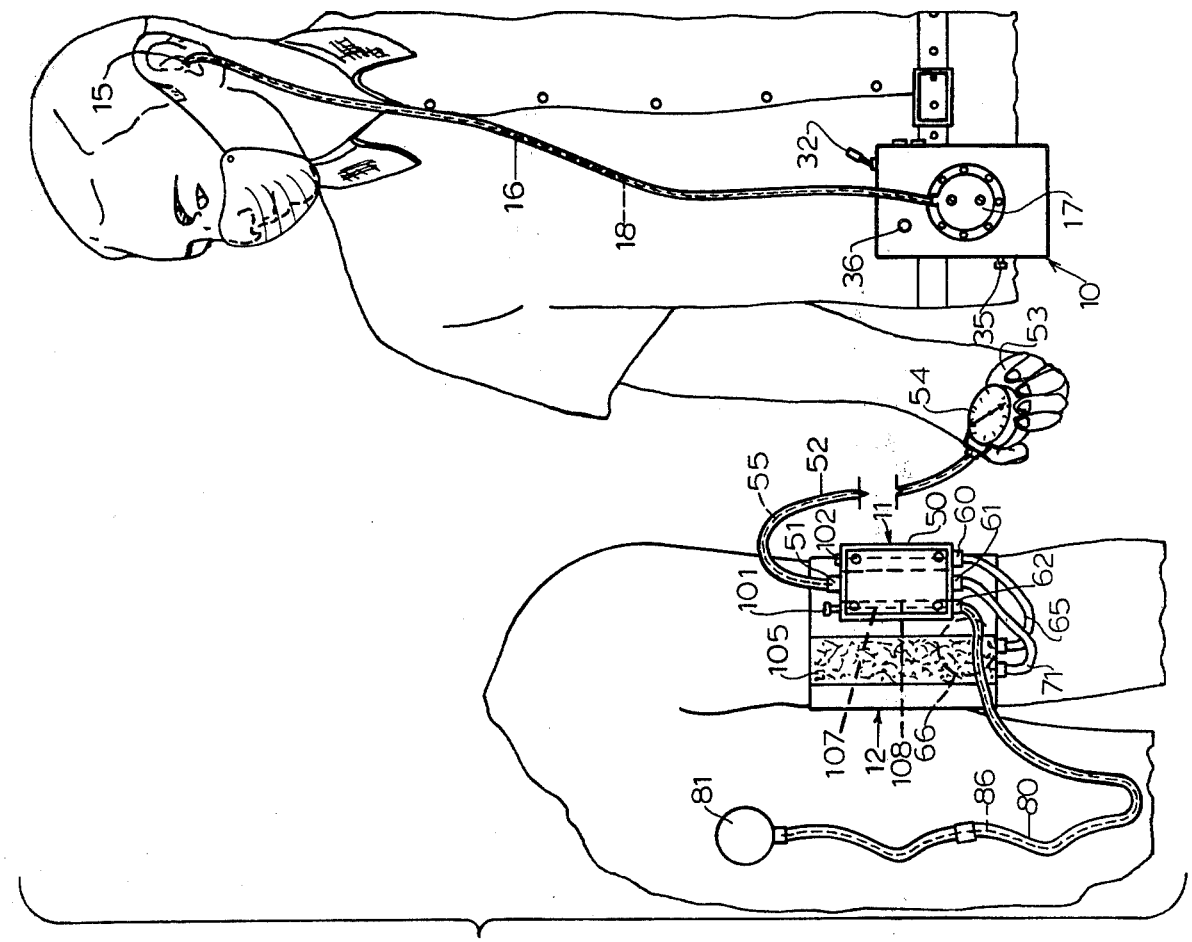
FIG. 4 is another view applicable to both embodiments of the system mounted on the patient and an anesthetist with the transmitter mounted on the cuff in a position designed to cause the transmitter to be on and with the transmitter and receiver antennas indicated in dashed lines and with the receiver mounted on the belt of the anesthetist.
Figure 5:
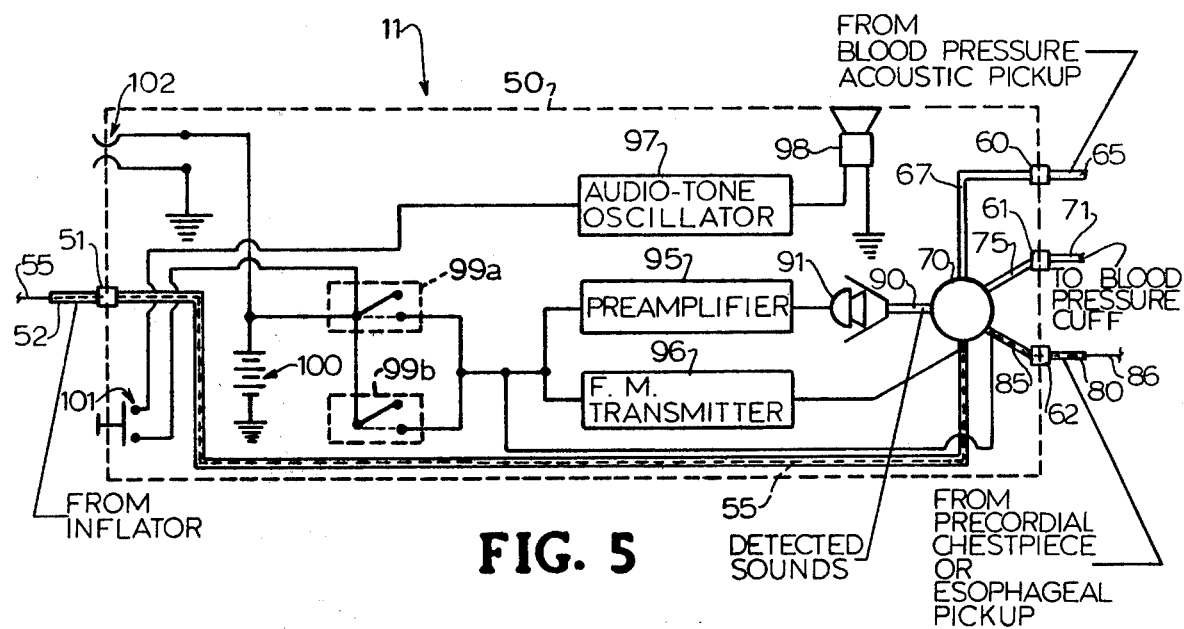
FIG. 5 is a block diagram of the transmitter unit according to a first embodiment.

For further reference, it may be noted that FIGS. 1-4, 6 and 7 are applicable to both embodiments, FIG. 5 illustrates the transmitter unit 11 of the first embodiment, FIG. 8 illustrates transmitter unit 11' of the second embodiment and FIGS. 9-10 refer to a pressure switch also associated with the second embodiment. The description will first describe the overall system based on utilizing the transmitter 11 of the first embodiment. Later, the description will deal with the transmitter 11' of the second embodiment and its relation to the overall system.

Receiver unit 10 and transmitter unit 11 should preferably be constructed in a manner to minimize interfering frequencies and a frequency modulated system is preferred. Receiver unit 10 includes, for both of the described embodiments, a suitable earpiece 15 connected by a length of miniature air tubing 16 to the speaker or transducer 17 such that any sounds produced by speaker 17 are transmitted to earpiece 15 through conventional tubing 16. Tubing 16 is also used to loosely enclose in the lumen of the tube a quarter wave reception antenna 18 indicated by dashed lines in FIGS. 4 and 6.

Figure 6:
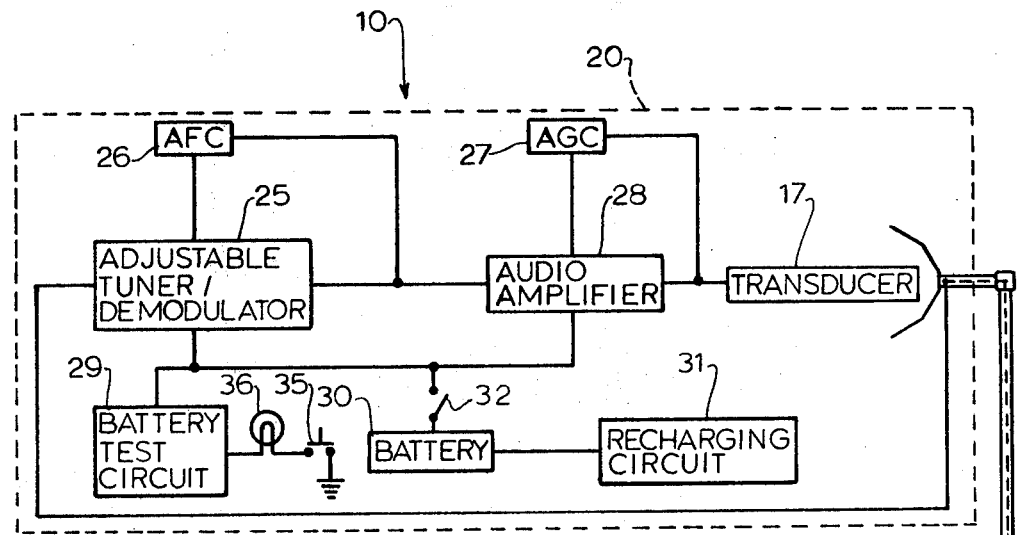
FIG. 6 is a block diagram of the receiver unit applicable to both embodiments.

Receiver unit 10 includes a suitable lightweight housing 20 which is designed to be worn on the anesthetist's belt (see FIGS. 1 and 4) or in a pocket (see FIG. 2). As best illustrated in FIG. 6, receiver unit 10 also includes adjustable tuner demodulator 25, automatic frequency control 26, automatic gain control 27, audio amplifier 28, battery test circuit 29, rechargeable battery 30, appropriate recharging circuit 31, on-off switch 32, battery test switch 35, and battery condition indicator lamp 36. The reception frequency may be adjustable, for example, between 88 and 108 MHz utilizing a thumb wheel adjustment accessible on the side of the receiver housing 20 (not shown) as is typical with miniature radio receivers. Thus, receiver unit 10 may be used with any number of transmitter units 11 operating on preassigned, fixed frequencies.

Transmitter unit 11 according to the first embodiment includes a small, lightweight housing 50, preferably formed from a nonferrous material, having a single luer-type plug 51 at one end for making a detachable connection to conventional inflator tubing 52 extending from inflator 53 secured adjacent pressure guage 54 according to conventional blood pressure measuring apparatus. Also to be noted is that pressure tube 52, extending between transmitter housing 50 and inflator 53, loosely enclosed in the lumen a quarter wave antenna 55 indicated by dashed lines in FIGS. 3, 4, 5 and 8.

Figure 3:
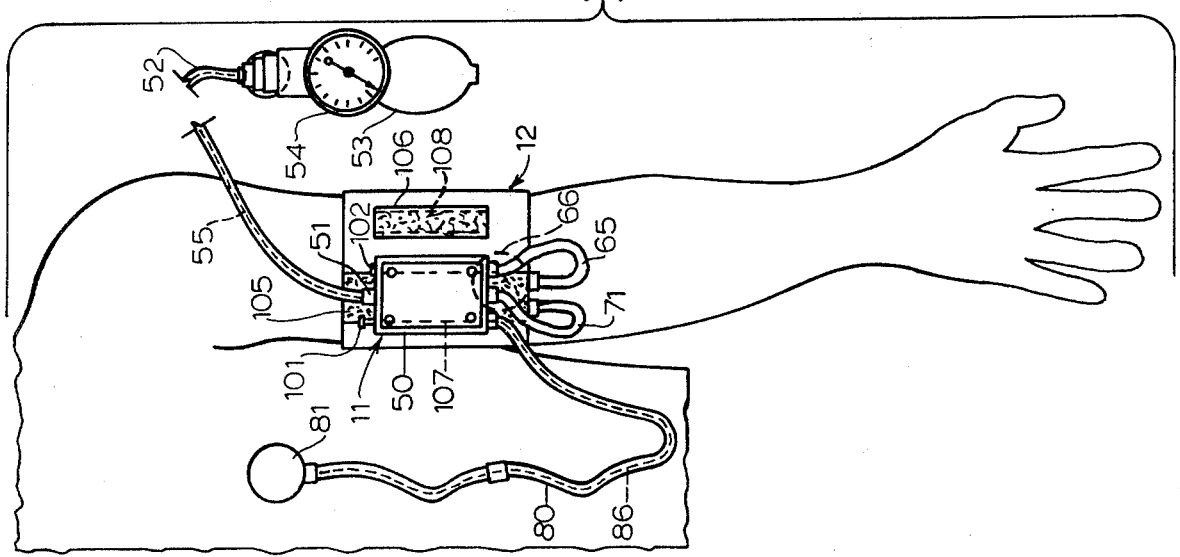
FIG. 3, applicable to both embodiments, illustrates the invention system with the transmitter unit mounted on the cuff at a position designed to maintain the transmitter unit in an off condition and with the transmitting antenna indicated in dashed lines enclosed in the lumen of the pressure and sound transmitting tubes.

Three additional luer-type plugs 60, 61, 62 mount at the opposite end of housing 50 of transmitter unit 11. Luer plug 60 provides a detachable connection for a small diameter, short length tube 65 extending between sound pickup head 66 and associated cuff unit 12 as illustrated in FIGS. 3 and 4. Thus, sounds associated with blood pressure measurements can be transmitted from sound pickup head 66 in cuff unit 12 through tubing 65 and connected tubing 67 (FIG. 5) to Ploss automatic switch valve 70 within transmitter unit 11 and whose operation is later described. Luer plug 61 connects through tubing 71 to cuff unit 12. A further section of tube 75 (FIG. 5) connects plug 61 with the previously-mentioned Ploss automatic switch valve 70 within transmitter unit 11. Luer plug 62 connects by means of tubing 80 to another sound pickup head which, as previously mentioned, may be either a chestpiece 81, i.e., precordial, or an esophagus pickup 79, i.e., esophageal. Quick disconnect 78 allows for ease in connecting either chestpiece 81 or esophagus pickup 79 to tubing 80. Thus, any sounds detected by pickup heads 79, 81 and which are transmitted through tube 80 can be transmitted through connecting tube 85 (FIG. 5) to Ploss automatic valve 70 within transmitter unit 11. Also to be noted here is that tube 80 provides a convenient means for enclosing in the lumen thereof another section of transmitting antenna 86 as indicated by dashed lines in FIGS. 3, 4, 5 and 8.

A commercially available Ploss automatic switch valve 70 is used in the described first embodiment, with a slightly modified standard blood pressure cuff 12. Ploss automatic switch valve 70 has five tubular connections therein. One connection provides a sound output to earpiece 15 being worn by the anesthetist to monitor the precordial or esophageal sounds. A second connection is used to receive pressure from inflator 53 whenever it is desired to inflate blood pressure cuff 12. A third connection receives blood pressure related sounds from blood pressure acoustic pickup 66. A fourth connection provides an outlet for pressure going to blood pressure cuff 12. The fifth connection provides means for receiving precordial related sounds from chestpiece 81 (FIGS. 1, 2 and 4) or esophageal pickup 79 (FIG. 2).

Referring more specifically to FIG. 5 illustrating transmitter 11 of the first embodiment, whenever blood pressure cuff unit 12 is not inflated, blood pressure related sounds are not generated and a sound path is established from precordial chestpiece 81 or esophageal pickup 79 through Ploss valve 70, through connecting tube 90 and to microphone 91. In this mode of operation, when cuff 12 is not inflated, the path between blood pressure acoustic pickup 66 and microphone 91 is still open but pickup 66 does not receive any sounds since cuff 12 is deflated. However, when it is desired to monitor blood pressure related sounds, the inflator 53 is utilized to pressurized tube 52 which connects through Ploss valve 70, tube 75 and tube 71 to blood pressure cuff unit 12 which acts to inflate cuff 12 and during which operation the pressure can be observed by means of pressure gauge 54. In this mode of operation, the sound transmission path between chestpiece 81 or esophageal pickup 79 and microphone 91 is closed off within Ploss valve 70 and another sound transmission path is established between blood pressure acoustic pickup 66, through tube 65, connecting tube 67, through Ploss valve 70, and through connecting tube 90 to microphone 91. Thus, with the described arrangement of the first embodiment depicted in FIG. 1, microphone 91 can be connected to monitor either blood pressure related sounds when blood pressure cuff unit 12 is inflated and to monitor chest or esophagus sounds whenever blood pressure cuff unit 12 is deflated.

With further reference to FIG. 5, transmitter unit 11 of the first embodiment includes within its housing 50 preamplifier 95, preferably having gain control, connected to microphone 91; FM transmitter 96; audio tone oscillator 97, with a connected speaker 98; a pair of magnet controlled reed switch arrangements 99a, 99b to be later explained; rechargeable battery power supply 100; battery and tone signal switch 101; and a recharging receptacle 102.

As best illustrated in FIGS. 3 and 4, transmitter unit 11 is arranged for convenient and detachable securement to cuff unit 12 which eliminates the need for auxiliary transmitter mounting apparatus. For this purpose and which is applicable to both embodiments, housing 50 of transmitter unit 11 and cuff unit 12 are fitted with mating Velcro pads. As illustrated in the described embodiment in FIGS. 3 and 4, cuff unit 12 is equipped with a relatively wide Velcro pad 105 and spaced therefrom a relatively narrow Velcro pad 106 in which a magnetized ferrous bar 108 is embedded. Housing 50 of transmitter unit 11 incorporates a mating Velcro pad indicated by dashed lines 107 in FIG. 3 and which shows Velcro pad 107 attached to Velcro pad 105 on cuff unit 12 corrsponding to transmitter unit 11 being in an inoperative stored position, i.e., remote from the actuating element.

When transmitter unit 11 is moved from the position shown in FIG. 3 to the position shown in FIG. 4, the magnetized ferrous bar 108 embedded in Velcro strap 106 on cuff unit 12 is placed in immediate proximity to reed switch arrangements 99a, 99b shown in FIGS. 5 and 8 and the normally open contacts are caused to close and thereby energize the circuitry illustrated in FIGS. 5 and 8 which places transmitter unit 11 in a transmitting condition. Reed switch arrangements 99a, 99b are horizontally mounted with respect to each other and at a right angle to each other. Two reed switch arrangements are provided in parallel to insure activation of transmitter unit 11 even though only one switch arrangement is closed. Such a situation might develop when transmitter housing 50 is not positioned in the most efficient position in respect to the magnetized bar 108. Normally, both switch arrangements would be closed but this arrangement insures activation of transmitter unit 11. Whenever it is desired not to use transmitter 11, it can be very quickly de-energized and stored by moving transmitter unit 11 back to the position depicted in FIG. 3. While the described reed switch arrangements 99a, 99b will be noted as having many advantages, recognition is given to the fact that an on-off switch properly wired could be used to accomplish the same function.

In operation, transmitter unit 11 is mounted on pressure cuff unit 12 in the manner depicted in FIG. 4. When blood pressure related sounds are desired to be monitored, blood pressure cuff unit 12 is inflated by means of inflator 53 during which the pressure increase is observed by means of gauge 54. During this monitoring of blood pressure related sounds, the related diastolic and systolic sounds are monitored by means of blood pressure sound pickup head 66 which transmits sounds throug Ploss valve 70 to microphone 91 for transmission utilizing antenna branches 55 and 86 located in tubes 52 and 80, respectively, as seen in FIG. 4. While not illustrated, it is recognized that the receiver unit and transmitter unit antennas could be constructed in a manner allowing for installation of the same within the receiver and transmitter housing respectively.

The mentioned sounds, in the form of radio signals, are received by receiver unit 10 through antenna 18 enclosed in the lumen of tube 16 and are transmitted to earpiece 15. During this pressure related sound measuring mode of operation, Ploss valve 70 acts to cut off any sounds originating in chestpiece 81 or esophageal pickup 79. In another mode of operation depicted in FIG. 2, the anesthetist is stationed within the vicinity of the patient but is not holding the pressure apparatus as in FIG. 1. In this mode, sounds from chestpiece pickup 81 or from esophageal pickup 79 are transmitted to Ploss valve 70 and then to microphone 91 for radio transmission by transmitter unit 11 to receiver unit 10. The sound transmission path from blood pressure acoustic pickup 66 through Ploss valve remains but transmits no blood pressure related sounds since none are being generated so that the only sounds reaching microphone 91 are those sounds picked up by chestpiece 81 or esophageal pickup 79. Note should be taken here that the mobility of the anesthetist is essentially unrestricted. Furthermore, there is no danger of extraneous noises being produced and amplified by the stethoscope lines getting tangled or hitting other equipment, as commonly experienced with the typical stethoscope arrangement used for monitoring patients during operations.

As and when tuning of transmitter 11 is required, test button 101 can be momentarily depressed with transmitter unit 11 installed as in FIG. 2 and which causes a test signal to be transmitted to receiver unit 10. The frequency of receiver unit 10 can be confirmed or modified as required in the event of the presence of conflicting frequencies in the operating environment.

Figure 7:
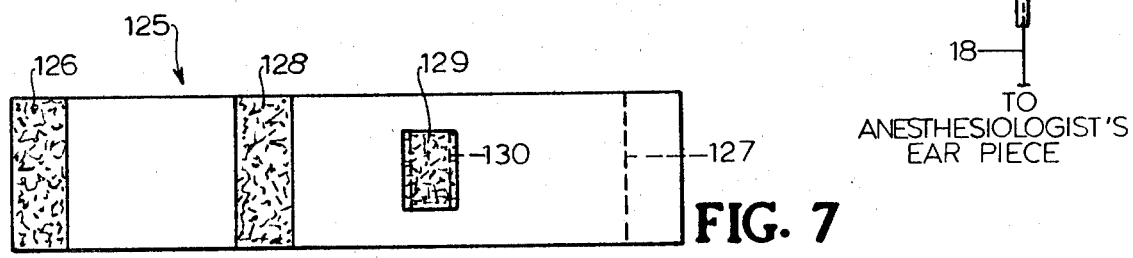
FIG. 7 is a plan view applicable to both embodiments of an auxiliary mounting device which allows the transmitter to be mounted on a standard blood pressure cuff in either of two positions, one of which utilizes an embedded magnet to actuate the transmitter.

While the patient monitoring apparatus of the present invention has been described in use with a slightly modified blood pressure cuff 12, the invention makes provision for use of a standard blood pressure cuff by wrapping the auxiliary band 125, illustrated in FIG. 7, about the standard cuff once in position on the arm of the patient. Band 125 has Velcro strips 126, 127 which are used to secure the band once wrapped in place. Velcro pad 128 corresponds to Velcro pad 105 of cuff 12 and mounts transmitter unit 11 in an inoperative position with the air of Velcro pad 107 incorporated on the back of housing 50. A Velcro strap 129 with embedded magnetized ferrous bar 130 corresponds to strap 106 and bar 108 of cuff 12. Thus, it can be seen that the very simple mounting and switching arrangement for transmitter 11 can be employed with a standard cuff in the manner previously explained by use of the auxiliary band 125.

As has already been mentioned, a second embodiment of the transmitter unit, designated as transmitter unit 11' is illustrated in FIGS. 8–10. Many of the components of transmitter unit 11 of the first embodiment are employed with the transmitter 11' of the second embodiment. Therefore, the same number designations are employed for the common parts of the two embodiments illustrated in FIGS. 5 and 8 respectively. Such common parts include the transmitter housing 50; the luer plug 51 for making a detachable connection to inflator tubing 52 extending from inflator 53; the antenna 55 but which in FIG. 8 is illustrated as being run in a slightly different array; luer plug 60 for providing a detachable connection with tube 65 extending between sound pickup head 66 and associated cuff unit 12 as illustrated in FIGS. 3 and 4; luer plug 61 for providing a connection through tubing 71 to cuff unit 2; luer plug 62 providing a connection for tubing 80 to another sound pickup head which, as previously mentioned, may be either a chestpiece 81, i.e., precordial, or an esophagus pickup 79, i.e., esophageal, as seen in FIG. 2; antenna 86 in tube 80; preamplifier 95; FM transmitter 96; audio tone oscillator 97; speaker 98; magnet controlled reed switch arrangements 99a, 99b; rechargeable battery power supply 100; battery and tone signal test switch 101; and a recharging receptacle 102.

In addition to the foregoing common parts, transmitter unit 11' of the second embodiment as illustrated in FIG. 8 includes a pressure actuated, single pole, double throw, switch 150 and a pair of microphones 155, 160. Switch 150 has a center tap 151 connected to preamplifier 95, a second tap 152 connected to microphone 155 and a third tap 153 connected to microphone 160. Switch 150 normally occupies the position indicated in FIG. 9 and, thus, normally maintains a connection between center tap 151 and the third tap 153. However, when pressure actuated, as illustrated in FIG. 10, the connection between center tap 151 and the third tap 153 is disconnected and a new connection is made between center tap 151 and the second tap 152. It will also be noted that tube 52 which connects to the inflator 53 also furnishes pressure through the tube section 52' and the tube branch 52" to switch 150 as well as to the blood pressure cuff 12 through the connecting tube 71. Thus, switch 150 is connected to the blood pressure cuff inflation system and is pressure actuated whenever the blood pressure cuff 12 is inflated. Also, in the arrangement illustrated in FIG. 8, it will be seen that microphone 155 has an established sound connection with the blood pressure cuff acoustic stethoscope pickup piece 66 while the other microphone 160 has an established sound connection with the chest mounted acoustic stethoscope 80, 81 or the esophageal pickup 79. However, no electronic detector contacts the patient.

From the foregoing description, it will be seen that the second embodiment as illustrated by FIGS. 8–10 provides for the transmitter 96 to be selectively coupled to the audio frequency output of either the microphone 155 which is coupled to the blood pressure acoustic pickup or to microphone 160 which is coupled to the precordial chestpiece or esophageal pickup, dependent on the status of the pressure actuated switch 150 which, in turn, is controlled by inflation or deflation of the blood pressure cuff 12. When the blood pressure cuff 12 is inflated, the electrical connection between the transmitter 96 and the microphone 160 associated with the precordial chestpiece or esopheageal pickup is open. At the same time, the electrical connection between the transmitter 96 and the microphone 155 associated with the blood pressure acoustic pickup is closed. Thus, when a blood pressure determination is being made, the pressure actuated switch 150 operates to interrupt the detection, amplification, and transmission of sounds associated with cardiorespiratory function while simultaneously allowing for the normal detection, amplification and radio transmission of blood pressure related sounds to the receiver unit 10 for monitoring by the anesthetist. However, when blood pressure is not being measured, the pressure actuated switch 150 acts to interrupt the detection, amplification and transmission of blood pressure related sounds while simultaneously allowing for the normal detection, amplification and radio transmission of sounds associated with cardiorespiratory function. From this explanation, it can be seen then that with the second embodiment, as with the first embodiment, the sounds of biologic function are selectively and automatically broadcast to the receiver unit 10 for monitoring and clinical interpretation.

In summary, many of the advantages of the patient monitoring system of the invention have been demonstrated. In particular, utilization of either the Ploss-type valve configuration, as illustrated by FIG. 5, or the pressure actuated switch configuration, as illustrated by FIG. 8, provides a convenient and reliable means for isolating and separately monitoring blood pressure sounds as well as chest sounds. Also, the reed switch and Velcro mounting arrangement provides a unique means for switching the transmitter unit on and off as well as providing a unique means for storing the transmitter unit when inoperative. Of particular advantage to the anesthetist is the fact that many of the typical extraneous noises which are produced and amplified by the conventional stethoscope arrangement are no longer encountered which provides a more comfortable operating environment. Of significant importance is the mobility allowed the anesthetist during those times when blood pressure is not being monitored. Also, the relatively fragile and expensive microphone apparatus is shielded from mechanical stress or damage, since the invention provides in both embodiments for the microphone apparatus to be mounted within and protected by the transmitter housing. Also, the invention eliminates the need to utilize microphones or other electronic detectors which are in intimate contact with the patient.

Another significant and important advantage of the invention resides in the fact that the transmitter unit in either of the illustrated embodiments can be utilized with any already-owned or available precordial, esophageal and pneumatic blood pressure cuff stethoscope equipment. The conventional inflator and pressure gauge also represent equipment which is normally owned or available to the clinician and which may be readily incorporated into the system of the invention. While the pressure bulb is believed to be the most widely used and the most commonly available inflation device, it will also be apparent that the system of the invention can adapt to any form of inflation device, whether it can be mechanical, electronic, automatic, semi-automatic or combinations of the same. Of course, the pressure gauge could also be mechanical, electronic or in the nature of a fluidic-type display.

Finally and of significant importance, it is to be recognized that the invention system basically provides a means for extending the operator's senses and aiding the operator in clinically assessing the patient's physiologic response to anesthesia and with remote and faithful reproduction of biologic sounds of diagnostic importance.

While described in connection with use by an anesthetist, it will be apparent that such term should be construed in a broad sense. Applications by operators other than anesthetists, i.e., doctors, nurses and other personnel, in an out of surgical environments are thus intended to be included within the scope of the invention. It is also recognized that while the invention is expected to derive its greatest benefit when employed to monitor both blood pressure related as well as other body related sounds, many advantages of the invention may be derived when only blood pressure related sounds are of interest and being monitored. Also recognized is that the novel transmitter unit of the invention may be employed with receiver units other than of the type described.

What is claimed is:

1. A portable patient monitoring apparatus adapted to permit, under control of the operator, selective detection and radio transmission of either a source of blood pressure related sounds or a source of other biologic sounds, comprising:
   (a) a receiver unit having a housing adapted for support on an operator's belt, pocket, or the like, and enclosing a tunable receiving circuit, power supply and a speaker, an antenna associated with said receiving circuit, and an earpiece and tubing between said speaker and earpiece for transmission of audible sounds from said speaker to said earpiece in response to transmitted signals received by said antenna;
   (b) a blood pressure cuff assembly mountable on a limb of the patient and including a blood pressure cuff, a first associated acoustic pickup piece for receiving and transmitting through associated tubing audible blood pressure related sounds developed when said cuff is inflated and inflating means for said cuff;
   (c) a second acoustic pickup piece suitable for positioning on said patient for receiving and transmitting through associated tubing other audible related body sounds; and
   (d) a transmitter unit having a housing adapted for support proximate the patient being monitored and enclosing a tunable radio transmitting circuit having a power supply and a microphone connected to said circuit for receiving sounds to be transmitted, an antenna associated with said transmitting circuit and a pressure controllable valve enclosed by said housing, said first and second acoustic pickup pieces being interconnected with said microphone by means of tubes which pass through said valve, said blood pressure cuff and said inflating means being interconnected by means of tubes which also pass through said valve and said valve being capable of closing off the audible sound interconnection between said microphone and first acoustic pickup piece upon inflation of said blood pressure cuff thereby enabling said operator to selectively control reception of sound by said microphones from either of said pickup pieces and thereby control selective transmission and reception by said transmitter and receiver units of either said blood pressure related or said other body sounds.

2. A patient monitoring apparatus as claimed in claim 1 wherein said second pickup piece comprises a precordial sound pickup piece adapted for being placed on the chest wall of the patient for auditory monitoring of chest-related cardiorespiratory sounds.

3. A patient monitoring apparatus as claimed in claim 1 wherein said second pickup piece comprises an esophageal sound pickup piece adapted to be placed in the esophagus of the patient directly behind the trachea or "windpipe" for auditory monitoring of cardiorespiratory sounds.

4. A patient monitoring apparatus as claimed in claim 1 wherein said valve provides a first air path detachably connected through tubing on one side with said inflating means and on another side detachably connected through tubing with said cuff, a second air path connected on one side through tubing to said first pickup piece and on the other side through tubing to said microphone, and a third air path detachably connected on one side through tubing to said second pickup piece and on the other side through tubing to said microphone.

5. A patient monitoring apparatus as claimed in claim 4 wherein said valve is effective when said inflating means is operated to permit pressurizing of said cuff through said first path and in said mode to close said third path and to connect said microphone to said first pickup piece through said second path for receiving sounds associated with measuring the blood pressure of the patient and developing therefrom radio signals broadcast from said transmitting antenna to said receiving antenna for monitoring as corresponding audio signals in said earpiece and said valve being effective when said cuff is not inflated to open said third path to connect said microphone to said second pickup piece through said third path for receiving sounds associated with the area where said second pickup piece is placed on the patient, such as chest, esophagus, or like sounds, and developing therefrom radio signals broadcast from said transmitting antenna to said receiving antenna for monitoring as corresponding audio signals in said earpiece.

6. A patient monitoring apparatus as claimed in claim 1 wherein at least a portion of said receiving circuit antenna is loosely enclosed within said earpiece tubing associated with said receiver unit.

7. A patient monitoring apparatus as claimed in claim 1 wherein at least a portion of said transmitting circuit antenna is loosely enclosed in selected portions of air path tubing associated with said transmitter unit.

8. A patient monitoring apparatus as claimed in claim 1 wherein at least a portion of said receiving circuit antenna is loosely enclosed within said earpiece tubing associated with said receiver unit and at least a portion of said transmitting circuit antenna is loosely enclosed in selected portions of air path tubing associated with said transmitter unit.

9. A patient monitoring apparatus as claimed in claim 1 wherein on-off operation of said transmitter unit is controlled by normally open switch means operable by an associated external actuating element and including mating releasable mounting means associated with said cuff assembly and transmitter housing providing a first releasable mounting position on said cuff assembly where said switch means is located remote from any external actuating element and a second releasable mounting position on said cuff assembly having a said actuating element where said switch means may be located proximate to and actuated by such actuating element to close and thereby turn said transmitter on.

10. A patient monitoring apparatus as claimed in claim 9 wherein said switch means comprises a pair of normally open reed switches connected in parallel, mounted horizontally and at right angles with respect to each other within said transmitter housing thereby adapting said transmitter unit to be turned on upon closing either one of such pair of reed switches.

11. A patient monitoring apparatus as claimed in claim 9 wherein said blood pressure cuff assembly includes a mating auxiliary band member adapted to be wrapped about and to be releasably secured on the outer surface of said cuff assembly and wherein said auxiliary band member includes said releasable mounting means and provides said first and second mounting positions.

12. A portable patient monitoring apparatus adapted to permit, under control of the operator, selective detection and radio transmission of either a source of blood pressure related sounds or a source of other biologic sounds, comprising:
  (a) a receiver unit having a housing adapted for support on an operator's belt, pocket, or the like, and enclosing a tunable receiving circuit, power supply and a speaker, an antenna associated with said receiving circuit, and an earpiece and tubing between said speaker and earpiece for transmission of audible sounds from said speaker to said earpiece in response to transmitted signals received by said antenna;
  (b) a blood cuff assembly mountable on a limb of the patient and including a blood pressure cuff, a first associated acoustic pickup piece for receiving and transmitting through associated tubing audible blood pressure related sounds developed when said cuff is inflated and inflating means for said cuff;
  (c) a second acoustic pickup piece suitable for positioning on said patient for receiving and transmitting through associated tubing other audible related body sounds; and
  (d) a transmitter unit having a housing adapted for support proximate the patient being monitored and enclosing a tunable radio transmitter circuit having a power supply and first and second microphones connected in a manner enabling either to receive audible sounds to be transmitted, an antenna associated with said transmitter circuit, said first microphone having an air path connection through tubing to said first pickup piece and said second microphone having an air path connection through tubing to said first pickup piece and said second microphone having an air path connection through tubing to said second pickup piece, and pressure actuated switch means enclosed by said housing and capable of establishing a connection between said first microphone and said transmitter circuit upon inflation of said blood pressure cuff and being capable of disconnecting the circuit between said first microphone and said transmitter circuit when said blood pressure cuff is deflated and simultaneously establishing a connection between said second microphone and said transmitter circuit thereby enabling said operator to selectively control reception of sound by said first and second microphones and thereby control selective transmission and reception by said transmitter and receiver units of either said blood pressure related or said other body sounds.

13. A patient monitoring apparatus as claimed in claim 12 wherein on-off operation of said transmitter unit is controlled by normally open switch means operable by an associated external actuating element and including mating releasable mounting means associated with said cuff assembly and transmitter housing providing a first releasable mounting position on said cuff assembly where said switch means in located remote from any external actuating element and a second releasable mounting position on said cuff assembly having a said actuating element where said switch means may be located proximate to and actuated by such actuating element to close and thereby turn said transmitter on.

14. A portable patient monitoring apparatus adapted to permit, under control of the operator, selective detection and radio transmission of either a source of blood pressure related sounds or a source of other biologic sounds, comprising:
- (a) a receiver unit having a housing adapted for support on an operator's belt, pocket, or the like, and enclosing a tunable receiving circuit, power supply and a speaker, an antenna associated with said receiving circuit, and an earpiece and tubing between said speaker and earpiece for transmission of audible sounds from said speaker to said earpiece in response to transmitted signals received by said antenna;
- (b) a blood pressure cuff assembly mountable on a limb of the patient and including a blood pressure cuff, a first associated acoustic pickup piece for receiving and transmitting through associated tubing audible blood pressure related sounds developed when said cuff is inflated and inflating means for said cuff;
- (c) a second acoustic pickup piece suitable for positioning on said patient for receiving and transmitting through associated tubing other audible related body sounds; and
- (d) a transmitter unit having a housing adapted for support proximate the patient being monitored and enclosing a tunable radio transmitter circuit having a power supply and microphone means for receiving sounds to be transmitted, an antenna associated with said transmitting circuit and pressure dependent operator means enclosed within said transmitter housing, said acoustic pickup pieces being sound connected with said microphone means by means of tubes which extend between said pickup pieces and said microphone means, said blood pressure cuff and said inflating means being interconnected by means of tubing which also passes at least partially through said housing and connects to said operator means, said operator means being capable of allowing the transfer of audible sounds from said first pickup piece through said microphone means to said transmitting circuit upon inflation of said pressure cuff and being capable of blocking such transmission upon deflation of said blood pressure cuff.

15. A patient monitoring apparatus as claimed in claim 14 wherein on-off operation if said transmitter unit is controlled by normally open switch means operable by an associated external actuating element and including mating releasable mounting means associated with said cuff assembly and transmitter housing providing a first releasable mounting position on said cuff assembly where said switch means is located remote from any external actuating element and a second releasable mounting position on said cuff assembly having a said actuating element where said switch means may be located proximate to and actuated by such actuating element to close and thereby turn said transmitter on.

16. A patient monitoring apparatus adapted to permit, under control of the operator, selective detection and radio transmission of a source of blood pressure related sounds, comprising:
- (a) a receiver unit having a tunable receiving circuit, power supply, an antenna and speaker, said speaker being adapted to produce audible sounds in response to transmitted signals received by said antenna;
- (b) a blood pressure cuff assembly mountable on a limb of the patient and including a blood pressure cuff, an associated acoustic pickup piece for receiving and transmitting through associated tubing audible blood pressure related sounds developed when said cuff is inflated and inflating means for said cuff; and
- (c) a transmitter unit adapted for support proximate the patient being monitored and having a tunable radio transmitter circuit having a power supply and microphone means for receiving sounds to be transmitted, an antenna associated with said transmitting circuit and pressure dependent operator means, said acoustic pickup piece being sound connected with said microphone means by means of tubing extending between said pickup piece and said microphone means, said blood pressure cuff and said inflating means being interconnected by means of tubing which also connects to said operator means, said operator means being capable of allowing the transfer of audible sounds from said pickup piece through said microphone means to said transmitting circuit upon inflation of said pressure cuff and being capable of blocking such transmission upon deflation of said blood pressure cuff.

17. A patient monitoring apparatus as claimed in claim 16 wherein on-off operation of said transmitter unit is controlled by normally open switch means operable by an associated external actuating element and including mating releasable mounting means associated with said cuff assembly and transmitter housing providing a first releasable mounting position on said cuff assembly where said switch means is located remote from any external actuating element and a second releasable mounting position on said cuff assembly having a said actuating element where said switch means may be located proximate to and actuated by such actuating element to close and thereby turn said transmitter on.

* * * * *

UNITED STATES PATENT OFFICE
CERTIFICATE OF CORRECTION

Patent No. 4,248,241           Dated February 3, 1981

Inventor(s) Ernest J. Tacchi

It is certified that error appears in the above-identified patent and that said Letters Patent are hereby corrected as shown below:

In Abstract, line 15, "cardiorespirtory" should read --cardiorespiratory--.

Col. 1, line 64, "assocaited" should read --associated--.

Col. 4, line 14, after the word "and" insert the word --the--.

Col. 4, lines 54-58, delete the sentence "However, the electronic connection between the radio frequency transmission circuitry and the microphone element associated with the chest or esophagus mounted acoustic stethoscope is opened".

Col. 5, line 26, "end" should read --and--.

Col. 7, line 62, "pressurized" should read --pressurize--.

Col. 9, line 4, "throug" should read --through--.

Col. 9, line 54, "air" should read --aid--.

Col.10, line 9, "unit 2" should read --unit 12--.

Col.11, line 67, "in an" should read --in and--.

Col.12, line 53, "microphones" should read --microphone--.

UNITED STATES PATENT OFFICE

CERTIFICATE OF CORRECTION

Patent No. 4,248,241     Dated February 3, 1981

Inventor(s) Ernest J. Tacchi

It is certified that error appears in the above-identified patent and that said Letters Patent are hereby corrected as shown below:

Col. 14, lines 40-42, delete "first pickup piece and said second microphone having an air path connection through tubing to said".

Col. 15, line 50, "if" should read --of--.

Signed and Sealed this

Twenty-fifth Day of August 1981

[SEAL]

Attest:

GERALD J. MOSSINGHOFF

Attesting Officer     Commissioner of Patents and Trademarks